United States Patent
Tagami et al.

(10) Patent No.: US 10,117,429 B2
(45) Date of Patent: Nov. 6, 2018

(54) METHOD FOR PRODUCING A PESTICIDAL COMPOSITION

(71) Applicant: SUMITOMO CHEMICAL COMPANY, LIMITED, Tokyo (JP)

(72) Inventors: Manabu Tagami, Kobe (JP); Nobuhito Ueda, Chiba (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 28 days.

(21) Appl. No.: 15/619,310

(22) Filed: Jun. 9, 2017

(65) Prior Publication Data

US 2017/0273299 A1 Sep. 28, 2017

Related U.S. Application Data

(63) Continuation of application No. 11/886,766, filed as application No. PCT/JP2006/301809 on Jan. 27, 2006, now abandoned.

(30) Foreign Application Priority Data

Mar. 28, 2005 (JP) ................. 2005-091274
Sep. 30, 2005 (JP) ................. 2005-286831

(51) Int. Cl.
*A01N 25/26* (2006.01)

(52) U.S. Cl.
CPC .................... *A01N 25/26* (2013.01)

(58) Field of Classification Search
CPC ........ A01N 25/26; A01N 51/00; A01N 25/10; A01N 43/40; A01N 43/56; A01N 25/08; A01N 25/12; A01N 25/00; A01C 1/06
See application file for complete search history.

(56) References Cited

U.S. PATENT DOCUMENTS

| 4,223,070 A | 9/1980 | Hahn et al. |
|---|---|---|
| 5,788,991 A | 8/1998 | Nastke et al. |
| 6,210,625 B1 | 4/2001 | Matsushita et al. |
| 2002/0054897 A1* | 5/2002 | Inoue ................. A01N 25/26 424/405 |
| 2004/0266626 A1 | 12/2004 | Schrof et al. |

FOREIGN PATENT DOCUMENTS

| EP | 0 847 691 A1 | 6/1998 |
|---|---|---|
| EP | 0 940 171 A2 | 9/1999 |
| JP | 52-028942 | 3/1977 |
| JP | 59-206302 | 11/1984 |
| JP | 61-091101 | 5/1986 |
| JP | 11-005704 | 1/1999 |
| JP | 2000-128705 A | 5/2000 |
| JP | 2001-181109 | 7/2001 |
| JP | 2002-234789 | 8/2002 |
| JP | 2003-286109 A | 10/2003 |
| JP | 2004-224609 | 8/2004 |
| WO | WO-91/10362 | 7/1991 |
| WO | WO-02/083290 A1 | 10/2002 |

OTHER PUBLICATIONS

Supplementary Search Report issued in EP 06712952.8, dated Jul. 4, 2008.
Office Action issued in EP 06 712952.8, dated Dec. 23, 2009, 3 pages.
Office Action (with English Translation) in CN 200680009709.1, dated Mar. 16, 2010.
Office Action in AU 2006229012 dated Aug. 31, 2010.
Office Action (with English Translation) in CN 200680009709.1 dated Sep. 26, 2010.
Rejection Decision (Translation) in CN 200680009709.1 dated Mar. 2, 2011.
Office Action (with English Translation) in JP 2006-052084, dated Oct. 25, 2011.
Office Action in IN 3381/KOLNP/2007 dated Dec. 21, 2011.
Reexamination Notice in CN 200680009709.1 dated Oct. 17, 2012.
Rejection Decision which issued in CN 201310236665.8 dated Jul. 2, 2015.
Reexamination Notification issued in CN 201310236665.8, dated Mar. 2, 2016.
Reexamination Decision issued in CN 201310236665.8 dated Apr. 28, 2016.

* cited by examiner

*Primary Examiner* — Audrea B Coniglio
(74) *Attorney, Agent, or Firm* — Foley & Lardner LLP

(57) ABSTRACT

A granular pesticidal composition in which a powdery pesticide is aggregated and coated with a thermosetting resin is capable of enabling a pesticidal active ingredient to be controlled-released. Further, the controlled-release pesticidal granule can be produced by mixing a powdery pesticide with a first liquid component serving as a raw material for a thermosetting resin, a process of adding a second liquid component serving as a raw material for a thermosetting resin, and then making the first liquid component react with the second liquid component to produce a thermosetting resin.

12 Claims, No Drawings

METHOD FOR PRODUCING A PESTICIDAL COMPOSITION

TECHNICAL FIELD

The present invention relates to a pesticidal composition containing an active ingredient in a controlled-release form.

BACKGROUND ART

Conventionally, there are variously suggested pesticidal formulations capable of enabling a pesticidal active ingredient to be sustainedly released for the purpose of continuance of the efficacy, decrease of phytotoxicity, and the like. As such controlled-release pesticidal formulations, there are known microencapsulated formulations, pesticidal granules coated with a thermosetting resin (JP 11-5704A), formulations obtained by mixing a pesticidal active ingredient and a urethane resin (JP 52-28942A), and the like.

DISCLOSURE OF THE INVENTION

The present invention provides a pesticidal composition containing a pesticidal active ingredient in a controlled-release form.

Also, the present invention provides a method for producing a pesticidal composition containing a pesticidal active ingredient in a controlled-release form.

The present invention is directed to a granular pesticidal composition in which a powdery pesticide is aggregated and coated with a thermosetting resin. This pesticidal granule is produced, for example, as described below. That is, the production method contains a process of mixing a powdery pesticide with a first liquid component serving as a raw material for a thermosetting resin, a process of subsequently adding thereto a second liquid component serving as a raw material for a thermosetting resin, a process of obtaining a pesticidal granule by making the first liquid component react with the second liquid component to produce a thermosetting resin, and a process of further adding to the resultant pesticidal granule the first liquid component and the second liquid component simultaneously or sequentially and making them react for coating of the pesticidal granule with the thermosetting resin.

In the present invention, the powdery pesticide may be an only pesticidal active ingredient in the form of powder, and usually is a powdery composition containing a pesticidal active ingredient and a diluting agent, generally having an average particle size (volume median diameter) of 100 μm or less, particularly 1 to 100 μm, preferably 1 to 30 μm.

The average particle size can be measured by a laser diffraction particle size analyzer such as MASTERSIZER 2000 manufactured by MALVERN and the like.

Generally mentioned as the pesticidal active ingredient are solid insecticidal compounds, insect growth regulating compounds, fungicidal compounds, herbicidal compounds, plant growth regulating compounds, insect repellents and the like, and specific examples thereof include compounds shown below. These are solid at ordinary temperature (20° C.), however, preferable are compounds having higher melting point which are solid, for example, at 50° C.

The insecticidal compounds and insect growth regulating compounds include pyrethroid compounds such as deltamethrin, tralomethrin, acrinathrin and tetramethrin; carbamate compounds such as propoxur, isoprocarb, xylylcarb, metolcarb, XMC, carbaryl, pyrimicarb, carbofuran, methomyl and phenoxycarb; organophosphorus compounds such as acephate, trichlorfon, tetrachlorvinphos, dimethylvinphos, pyridafenthion, azinphos-ethyl and azinphos-methyl; urea compounds such as diflubenzuron, chlorofluazuron, lufenuron, hexaflumuron, flufenoxuron, flucycloxuron, cyromazine, diafenthiuron, hexythiazox, novaluron, teflubenzuron, triflumuron, 4-chloro-2-(2-chloro-2-methylpropyl)-5-(6-iodo-3-pyridylmethoxy)pyridazin-3(2H)-one, 1-(2,6-difluorobenzoyl)-3-[2-fluoro-4-(trifluoromethyl)phenyl]urea, 1-(2,6-difluorobenzoyl)-3-[2-fluoro-4-(1,1,2,3,3,3-hexafluoropropoxy)phenyl]urea, 2-tert-butylimino-3-isopropyl-5-phenyl-3,4,5,6-tetrahydro-2H-1,3,5-thiadiazon-4-one and 1-(2,6-difluorobenzoyl)-3-[2-fluoro-4-(1,1,2,2-tetrafluoroethoxy)phenyl]urea; neonicotinoid compounds such as imidacloprid, acetamiprid, clothianidin, nitenpyram and diacloden; cartap, buprofezin, thiocyclam, bensultap, phenoxycarb, fenezaquin, fenpyroximate, pyridaben, hydramethylnon, thiodicarb, chlorfenapyr, fenproxymate, pymetrozine, pyrimidifen, tebufenozide, tebufenpyrad, triazamate, indoxacarb, sulfluramid, milbemectin, ivermectin, boric acid, p-dichlorobenzene and the like.

The fungicidal compounds include benzimidazole compounds such as benomyl, carbendazim, thiabendazol and thiophanate-methyl, and precursors thereof; phenyl carbamate compounds such as diethofencarb; dicarboxyimide compounds such as procymidone, iprodione and vinclozolin; azole compounds such as diniconazole, probenazole, epoxyconazole, tebuconazole, difenoconazole, cyproconazole, flusilazole and triadimefon; acylalanine compounds such as metalaxyl; carboxamide compounds such as furametpyr, mepronil, flutolanil and trifluzamide; organophosphorus compounds such as triclofos-methyl, fosetyl-aluminum and pyrazophos; anilinopyrimidine compounds such as pyrimethanil, mepanipyrim and cyprodinil; cyanopyrrole compounds such as fludioxonil and fenpiclonil; antibiotics such as blastocidin S, kasugamycin, polyoxin and validamycin; methoxyacrylate and methoxyacrylamide compounds such as azoxystrobin, kresoxim-methyl and metominostrobin; chlorothalonil, mancozeb, captan, folpet, tricyclazole, pyroquilon, probenazole, fthalide, cymoxanil, dimethomorph, acibenzolar-S-methyl, famoxadone, oxolinic acid, fluazinam, ferimzone, diclocymet, chlobenthiazone, isovaledione, tetrachloroisophthalonitrile, thiophthalimide-oxybisphenoxyarsine, 3-iodo-2-propylbutyl carbamate, p-hydroxybenzoate, sodium dehydoacetate, potassium sorbate, and the like.

The herbicidal compounds include triazine compounds such as atrazine and metribuzin; urea compounds such as fluometuron and isoproturon; hydroxybenzonitrile compounds such as bromoxynil and ioxynil; 2,6-dinitroaniline compounds such as pendimethaline and trifluralin; aryloxyalkanoic acid compounds such as 2,4-D, dicamba, fluroxypyr and mecoprop; sulfonylurea compounds such as bensulfuron-methyl, metsulfuron-methyl, nicosulfuron, primisulfuron-methyl and cyclosulfamuron; imidazolinone compounds such as imazapyr, imazaquin and imazethapyr; bispyribac-sodium, bisthiobac-sodium, acifluorfen-sodium, sulfentrazone, paraquat, flumeturam, triflusulfron-methyl, fenoxaprop-p-ethyl, diflufenican, norflurazone, isoxaflutole, ammonium glufosinate, glyphosate, bentazone, mefenacet, propanil, fluthiamide, flumiclorac-pentyl, flumioxazine and the like.

The plant growth regulating compounds include maleic hydrazide, chlormequat, ethephon, gibberellin, mepiquat chloride, thidiazuron, inabenfide, paclobutrazole, uniconazole and the like. The insect repellents include 1S,3R,4R, 6R-carane-3,4-diol, dipropyl 2,5-pyridine dicarboxylate and the like.

Even in the case of a liquid pesticidal active ingredient, it can be used, as a powdery pesticide which is a composition in the form of powder held on a diluent, in the present invention.

The diluent is a solid carrier to be used in a powdery pesticide, and includes mineral carriers, for example, kaolin minerals such as kaolinite, dickite, nacrite and halocite; serpentines such as chrysotile, lizartite, antigorite and amesite; montmorillonite minerals such as sodium montmorillonite, calcium montmorillonite and magnesium montmorillonite; smectites such as saponite, hectrite, sauconite and hyderite; micas such as pyrophyllite, talc, agalmatolite, white mica, phengite, sericite and illite; silica such as cristobalite, amorphous silica and quartz; magnesium silicate hydrate such as attapulgite and sepiolite; sulfate minerals such as gypsum; dolomite, calcium carbonate, zeolite, boiling stone, tuff, vermiculite, laponite, pumice, diatomaceous earth, acid clay, terra alba, and the like. These may be used singly or in combination of two or more.

The powdery pesticide may contain auxiliaries for pesticides such as diluents, surfactants, stabilizers, coloring agents, perfumes and the like, in addition to pesticidal active ingredients.

The surfactants include nonionic surfactants such as polyoxyethylene alkyl ethers, polyoxyethylene alkylaryl ethers, polyoxyethylene lanolin alcohols, polyoxyethylene alkylphenol formalin condensates, polyoxyethylene sorbitan fatty esters, polyoxyethylene glyceryl monofatty esters, polyoxypropylene glycol monofatty esters, polyoxyethylene sorbitol fatty esters, polyoxyethylene castor oil derivatives, polyoxyethylene fatty esters, higher fatty acid glycerin esters, sorbitan fatty esters, sucrose fatty esters, polyoxyethylene polyoxypropylene block polymers, polyoxyethylene fatty amide, alkylolamide and polyoxyethylene alkylamine; cationic surfactants such as alkylamine hydrochlorides (e.g., dodecylamine hydrochloride), alkyl quaternary ammonium salts (e.g., dodecyltrimethyl ammonium salt, alkyldimethylbenzyl ammonium salt, alkylpyridinium salt, alkylisoquinolinium salt, dialkylmorpholinium salt), benzethonium chloride and polyalkylvinylpyridinium salt; anionic surfactants such as sodium salts of fatty acid (e.g., sodium palmitate), sodium salts of ether carboxylic acid (e.g., sodium polyoxyethylene lauryl ether carboxylate), amino acid condensates of higher fatty acids (e.g., sodium lauroyl sarcosinate, sodium N-lauroylglutamate), higher fatty ester sulfonic acid salts (e.g., higher alkylsulfonate, lauric ester sulfonate), dialkylsulfosuccinic acid salt (e.g., dioctyl sulfosuccinate), higher fatty amide sulfonic acid salts (e.g., oleic amide sulfonate), alkylarylsulfonic acid salts (e.g., sodium dodecylbenzenesulfonate, diisopropylnaphthalenesulfonic acid salt), formalin condensate of alkylaryl sulfonic acid salt, higher alcohol sulfuric acid ester salts (e.g., pentadecane-2-sulfate), polyoxyethylene alkylphosphoric acid salts (e.g., dipolyoxyethylene dodecyl ether phosphate), styrene-maleic acid salt copolymer and the like; ampholytic surfactants such as N-laurylalanine, N,N,N-trimethylaminopropionic acid, N,N,N-trihydroxyethylaminopropionic acid, N-hexyl-N,N-dimethylaminoacetic acid, 1-(2-carboxyethyl)pyrimidinium betaine and lecithin.

The stabilizers include, for example, phenol antioxidants, amine antioxidants, phosphorus type antioxidants, sulfur type antioxidants, ultraviolet absorbers, epoxidized vegetable oils such as epoxidized soybean oil, epoxidized linseed oil and epoxidized rape seed oil; isopropylacid phosphate, liquid paraffin, ethylene glycol and the like.

The coloring agents include, for example, rhodamines such as rhodamine B and solar rhodamine, and colorants such as Yellow No. 4, Blue No. 1 and Red No. 2, and the perfumes include, for example, ester perfumes such as ethyl acetoacetate, ethyl enantate, ethyl cinnamate and isoamyl acetate, organic acid perfumes such as caproic acid and cinnamic acid, alcohol perfumes such as cinnamic alcohol, geraniol, citral and decyl alcohol, aldehydes such as vanillin, piperonal and perilaldehyde, ketone perfumes such as maltol and methyl β-naphthyl ketone, menthol, and the like.

When the powdery pesticide contains a diluent, the amount of pesticidal active ingredients in the powdery pesticide is usually 1 to 95 wt %, preferably 10 to 90 wt %, the amount of the diluent is usually 5 to 99 wt %, preferably 10 to 90 wt %. When the powdery pesticide contains auxiliaries for pesticides, the total amount of the auxiliaries for pesticides is usually 1 to 30 wt %, preferably 2 to 20 wt %.

The powdery pesticide is obtained by mixing and pulverizing a pesticidal active ingredient, if necessary, a diluent, further if necessary, auxiliaries for pesticides such as surfactants, stabilizers, coloring agents, perfumes and the like. Further, the powdery pesticide can also be obtained by mixing components pulverized previously into powdery form.

As the thermosetting resin for fixing the powdery pesticide, urethane resin, urea resin, urethane-urea resin, epoxy resin and the like are mentioned, and in the present invention, urethane resin is particularly preferable.

The pesticidal granule of the present invention has an average particle size (volume median diameter) of usually 1 to 200 μm, preferably 10 to 200 μm, more preferably 20 to 150 μm. The average particle size can be measured by a laser diffraction particle size analyzer such as MASTERSIZER 2000 manufactured by MALVERN and the like.

The thermosetting resin is obtained usually by making two different liquid components react, and the pesticidal granule of the present invention is produced, for example, by mixing a powdery pesticide with a first liquid component serving as a raw material of a thermosetting resin, then, adding thereto a second liquid component serving as a raw material for a thermosetting resin, making the first liquid component react with the second liquid component to produce a thermosetting resin, further if necessary, adding the first liquid component and the second liquid component simultaneously or sequentially and making them react to produce a thermosetting resin. By regulating the amounts of the first liquid component and the second liquid component, the thickness of a coat made of a thermosetting resin can be regulated, to change the degree of controlled-release to desirable degree. The first liquid component and the second liquid component are not each necessarily limited to that constituted only of one ingredient, and may also be a mixture.

When the thermosetting resin is a urethane resin, one of the first liquid component and the second liquid component is a polyol, and another is a polyisocyanate.

The polyol includes condensed polyester polyols, polyether polyols, polyacrylic acid polyols, polymethacrylic acid polyols, lactone type polyester polyols, polycarbonate polyols, natural polyol and denatured products thereof and the like. The condensed polyester polyol is usually obtained by a condensation reaction of a polyol with a dibasic acid. The polyether polyol is usually obtained by an addition-polymerization of propylene oxide or ethylene oxide to a polyvalent alcohol and the like. The polyacrylic acid polyol and polymethacrylic acid polyol are usually obtained by a condensation reaction of polyacrylic acid with polyol, a condensation reaction of polymethacrylic acid with polyol, a condensation reaction of acrylic acid with polyol, a condensation reaction of methacrylic acid with polyol, a polymerization reaction of an acrylate monomer, or a polymerization reaction of a methacrylate monomer. The lactone type polyester polyol is obtained by ring-opening polymerization of ε-caprolactone using a polyvalent alcohol as an initiator. The polycarbonate polyol is usually obtained by reaction of glycol with a carbonate, and the polyol includes methylene glycol, ethylene glycol, propylene glycol, tetramethylene glycol, hexamethylene diol, trimethylolpropane, polytetramethylene glycol, glycerin, and oligomers thereof, and the like.

As the polyol to be used in the present invention, branched polyols, and mixtures of a branched polyol and a linear polyol are preferable, and among the mixtures, preferable are those in which the number of hydroxyl groups derived from the linear polyol is 60% or less based on the hydroxyl groups present in the polyol. The branched polyol is a polyol having three or more hydroxyl groups in the molecule, and polyols having three hydroxyl groups in the molecule are preferable. The linear polyol is a polyol having two hydroxyl groups in the molecule, and usually has a hydroxyl group on each of both terminals of the molecule.

Preferable are the above-described linear polyol are linear polyols having an OH equivalent of 100 or less, and mixtures of a linear polyol having an OH equivalent of 100 or less and a linear polyol having an OH equivalent of 100 or more, and among the mixtures, preferable are those in which the number of hydroxyl groups derived from the linear polyol having an OH equivalent of 100 or more is 60% or less based on the hydroxyl groups present in the polyol. The linear polyols having an OH equivalent of 100 or less include ethylene glycol, propylene glycol, trimethylene glycol and the like.

The polyisocyanate includes toluene diisocyanate (TDI), diphenylmethane diisocyanate (MDI), naphthalene diisocyanate, tolylene diisocyanate, hexamethylene diisocyanate, isophorone diisocyanate, xylylene diisocyanate, 4,4-methylenebis(cyclohexyl isocyanate), trimethylhexamethylene diisocyanate, 1,3-(isocyanatomethyl)cyclohexane, triphenylmethane triisocyanate, tris(isocyanatophenyl) thiophosphate and the like. Instead of the above-described polyisocyanate monomers, denatured isocyanates and oligomers thereof can also be used providing that they have flowability. The denatured isocyanates include adduct denatured isocyanates, biuret denatured isocyanates, isocyanurate denatured isocyanates, block denatured isocyanates, prepolymer denatured isocyanates, dimerized denatured isocyanates, and the like. Polymethylene polyphenyl isocyanurate (polymeric MDI), which is obtained by condensing aniline and formalin and phosgenating the obtained polyamine, is preferable from the standpoint of easiness of reaction control and low vapor pressure and excellent workability.

The urethane resin is produced by making a polyol react with a polyisocyanate under heating, for example, at 40 to 100° C. In this operation, hardening catalysts such as organometals, amines and the like are added, if necessary.

The hardening catalysts include organometals such as dibutyltin diacetate, dibutyltin dichloride, dibutyltin dilaurate, dibutylthiostannic acid, stannous octylate, di-n-octyltin dilaurate and the like, triethylenediamine, N-methylmorpholine, N,N-dimethyldidodecylamine, N-dodecylmorpholine, N,N-dimethylcyclohexylamine, N-ethylmorpholine, dimethylethanolamine, N,N-dimethylbenzylamine, 1,8-diazabicyclo[5.4.0]undecene-7, isopropyl titanate, tetrabutyl titanate, oxyisopropyl vanadate, n-propyl zirconate, 1,4-diazabicyclo[2.2.2]octane and the like.

When the thermosetting resin is a urethane resin, any of polyol or polyisocyanate may be used as the first liquid component, and preferably, a polyol is used as the first liquid component and a polyisocyanate is used as the second liquid component. When a hardening catalyst is used, the hardening catalyst may be added to any of the first liquid component and the second liquid component, and preferably, added to the first liquid component.

When the thermosetting resin is a urea resin, one of the first liquid component and the second liquid component is a polyamine or water, and another is a polyisocyanate.

The polyisocyanate includes the above-described polyisocyantes, and the polyamine includes diethylenetriamine, triethylenetetramine and the like.

When thermosetting resin is a urea resin, any of polyamine, water or polyisocyanate may be used as the first liquid component, and it is preferable that a polyamine is used as the first liquid component and a polyisocyanate is used as the second liquid component. When water is used as the liquid component, it is usual that a polyisocyanate is used as the first liquid component and water is used as the second liquid component.

When the thermosetting resin is a urethane-urea resin, one of the first liquid component and the second liquid component is a mixture of a polyol and a polyamine, and another is a polyisocyanate. It is preferable that a mixture of a polyol and a polyamine is used as the first liquid component, and a polyisocyanate is used as the second liquid component.

When the thermosetting resin is an epoxy resin, one of the first liquid component and the second liquid component is a hardening agent, and another is a compound containing a glycidyl group.

The hardening agent is usually a polyamine, and the compound containing a glycidyl group includes usually polyglycidyl ether, polyglycidylamine and the like.

The polyamine includes diethylenetriamine, triethylenetetramine, m-xylylenediamine, isophoronediamine, methyliminobispropylamine, menthanediamine, m-phenylenediamine, diaminophenylmethane, diaminodiphenylsulfone, diaminodiethyldiphenylmethane, polyamide-denatured polyamine, ketone-denatured polyamine, epoxy-denatured polyamine, thiourea-denatured polyamine, Mannich-denatured polyamine, Michael addition-denatured polyamine and the like, and the compound containing a glycidyl group includes polyglycidyl ethers such as bisphenol A type polyglycidyl ether, bisphenol F type polyglycidyl ether, hydrogenated bisphenol A type polyglycidyl ether, naphthalene type polyglycidyl ether, brominated bisphenol A type polyglycidyl ether, bisphenol S type polyglycidyl ether, bisphenol AF type polyglycidyl ether, biphenyl type polyglycidyl ether, fluolein type polyglycidyl ether, phenol novolak type polyglycidyl ether, o-cresol novolak type polyglycidyl ether, DPP novolak type polyglycidyl ether, trishydroxyphenylmethane type polyglycidyl ether and tetraphenylolethane type polyglycidyl ether; and polyglycidylamines such as tetraglycidyldiaminodiphenylmethane type polyglycidylamine, hydantoin type polyglycidylamine, 1,3-bis(N,N-diglycidylaminomethyl)cyclohexane, aniline type polyglycidylamine, toluidine type polyglycidylamine, triglycidyl isocyanurate type polyglycidylamine and aminophenol type polyglycidylamine.

It is preferable that a polyamine is used as the first liquid component and a polyglycidyl ether or polyglycidylamine is used as the second liquid component.

The present invention provides also a method for producing a pesticidal composition containing a process of mixing a powdery pesticide with a first liquid component serving as a raw material for a thermosetting resin, a process of subsequently adding to this a second liquid component serving as a raw material for a thermosetting resin, and a process of reacting the first liquid component and the second liquid component to produce a thermosetting resin.

In the production method of the present invention, the viscosity of the first liquid component and the second liquid component is usually 2000 mPa·s or less.

When the thermosetting resin is a urethane resin, the viscosity of the polyol is 1000 mPa·s or less, more preferably 800 mPa·s or less (B type viscometer, 25° C., 12 rpm), and the viscosity of the polyisocyanate is 300 mPa·s or less, more preferably 200 mPa·s or less (B type viscometer, 25° C., 12 rpm).

The process of mixing a powdery pesticide with a first liquid component serving as a raw material for a thermosetting resin is generally carried out by adding a first liquid component to a vessel while rolling a powdery pesticide in the vessel under dry conditions wherein the powdery pesticide is not dispersed in a liquid medium. This process is carried out usually at 0 to 100° C., preferably at 10 to 80° C. From the standpoint of safety, the process is carried out preferably under a nitrogen atmosphere. As the method of rolling a powdery pesticide in a vessel, mentioned are, for example, a) a method in which a vessel of pan type or drum type containing a powdery pesticide is rotated around an inclined or horizontal axis, b) a method in which in a vessel containing a powdery pesticide, a stirring blade of approximately the same size as the diameter of the bottom part of the vessel is placed and rotated, and c) a method in which in a vessel containing a powdery pesticide, the powdery pesticide is rolled by air flow.

The subsequent process of adding to this a second liquid component serving as a raw material for a thermosetting resin is also carried out usually at 0 to 100° C., preferably at 10 to 80° C. From the standpoint of safety, the process is carried out preferably under a nitrogen atmosphere. The second liquid component is used in a proportion of usually 0.9 to 1.05 equivalents, preferably 0.95 to 1.00 equivalents based on one equivalent of the first liquid component.

If the thermosetting resin is a polyurethane resin and the first liquid component is a polyol, then, the second liquid component is a polyisocyanate, and it is advantageous to appropriately adjusting the amount of the polyisocyanate so that the amount of the polyisocyanate based on isocyanate group (NCO) is 0.8 to 1.1 equivalents, preferably 0.9 to 1.1 equivalents, further preferably 0.95 to 1.05 equivalents relative to one equivalent of polyol based on hydroxyl group (OH).

The process of reacting the first liquid component and the second liquid component to process a thermosetting resin is also carried out usually at 0 to 100° C., preferably at 40 to 80° C. From the standpoint of safety, the process is carried out preferably under a nitrogen atmosphere. In this process, it is preferable to carry out mixing while imparting shear force by a rotating blade to a powdery pesticide. More specifically mentioned is a method of stirring a powdery pesticide by a blade rotating at a rate of 50 to 3000 m/min, preferably 100 to 2000 m/min, more preferably 200 to 1000 m/min in terms of the speed of the leading edge of the blade. The stirring is usually carried out until an unhardened thermosetting resin is hardened completely and the resultant pesticide granule shows no stickiness. The stirring time may be varied depending on the kind of the thermosetting resin and the temperature of the procedure.

To the pesticide granule obtained as described above, the first liquid component and the second liquid component are added simultaneously or sequentially further if necessary, and these are reacted to produce a thermosetting resin, and this process is carried out once or repeated several times to increase the thickness of a coat made of the thermosetting resin and to promote mutual coagulation of particles, thereby, discharge of active ingredients can be delayed. That is, the discharge speed of active ingredients can be regulated in accordance with an object.

The amount of unhardened thermosetting resins to be added, namely, the total amount of the first liquid component and the second liquid component is usually 5 to 150 parts by weight, preferably 10 to 100 parts by weight, more preferably 25 to 80 parts by weight based on 100 parts by weight of a powdery pesticide.

As the specific vessel to be used in the production method of the present invention, there are mentioned NEWGRA-MACHINE manufactured by Seishin Kigyo K.K. as an apparatus in which particles manifest circular motion in the vessel along the outer periphery thereof, and HIGH SPEED MIXER and HIGH FLEX GRAR manufactured by Fukae Powtec K.K. as an apparatus equipped with an agitator of low revolution in a mixer and a chopper of high revolution on a side face, in which raw materials charged are mixed, dispersed and sheared in a short period of time by the action of both the blades. Further, HIGH SPEED MIXER manufactured by Freund Sangyo K.K., VERTICAL GRANULATOR manufactured by Powrex K.K., NEW SPEED MILL manufactured by Okada Seiko K.K., are mentioned as apparatuses showing the same performance.

Further, an apparatus described in JP 9-75703A can also be used.

In the production method of the present invention, there is no need of use of a solvent such as water and the like, thus, an operation of drying and the like is not necessary, consequently, a pesticidal granule containing an pesticidal active ingredient in a controlled-release manner can be produced easily.

The pesticidal granule of the present invention can be sprayed directly to pests to be controlled, or plants or soil to be protected, or diluted with water, and auxiliaries such as surfactants and the like are added if necessary to give a suspension, and the suspension is sprayed.

EXAMPLES

The present invention will be illustrated further in detail by the following examples, but the present invention is not limited to these examples.

In the following production examples, HIGH SPEED MIXER apparatus (LFS-GS-1J type, manufactured by Fukae Powtec K.K.) was used.

The HIGH SPEED MIXER apparatus is a stirring apparatus having a horizontal round dish type vessel part having an opening at an upper portion, an agitator blade rotating around a vertical line as the axis passing through the center of the bottom of the horizontal round dish type vessel part, and a chopper blade rotating around a horizontal line as the axis penetrating the side face of the vessel part, in which the vessel part has a content volume of about 2 L and an inner diameter of about 18 cm, and the agitator blade is composed of three blades having a radius of about 9 cm and attached to the bottom face so that the three blades can rotate along the bottom face and the inner walls of the vessel part. The chopper blade has two pairs of twin blades having a radius of 2 cm and attached rotatably to the side wall face of the vessel part so as not to come in tough with the bottom face of the vessel part and the agitator blade.

Reference Example 1 (Preparation of Powdery Pesticide 1)

45.5 parts by weight of 5-chloro-N-(1,3-dihydro-1,1,3-trimethyl-4-isobenzofuranyl)-1,3-dimethylpyrazole-4-carboxamide (common name: furametpyr) as a pesticidal active ingredient and 9 parts by weight of TOKUSEAL GU-N (amorphous silicon dioxide hydrate manufactured by Tokuyama Soda Co., Ltd.) and 45.5 parts by weight of bentonite FUJI (manufactured by Hojun K.K.) as diluents were mixed uniformly, and the mixture was all pulverized by a centrifugal pulverizer, to afford Powdery pesticide 1 having an average particle size of 5.0 μm (measured by MASTERSIZER 2000 manufactured by MALVERN).

Reference Example 2 (Preparation of Powdery Pesticide 2)

65 parts by weight of (E)-N-(6-chloro-3-pyridylmethyl)-N-ethyl-N'-methyl-2-nitrovinylidenediamine (common name: nitenpyram) as a pesticidal active ingredient and 35 parts by weight of SHOKOZAN Clay S (kaolin clay: manufactured by Shokozan Kogyosho K.K.) as a diluent were mixed uniformly, and the mixture was all pulverized by a centrifugal pulverizer, to afford Powdery pesticide 2 having an average particle size of 16.0 μm (measured by MASTERSIZER 2000 manufactured by MALVERN).

Reference Example 3 (Preparation of Polyol Premix 1)

54.1 parts by weight of SUMIFEN TM (branched polyether polyol manufactured by Sumika Bayer Urethane K.K.) and 45.9 parts by weight of SUMIFEN 1600U (linear polyether polyol manufactured by Sumika Bayer Urethane K.K.) were mixed uniformly to afford Polyol premix 1. The viscosity of Polyol premix 1 was 393 m·Pa (B type viscometer, 25° C., 12 rpm, Rotor No. 1).

Reference Example 4 (Preparation of Polyol Premix 2)

41.3 parts by weight of SUMIFEN TM (branched polyether polyol manufactured by Sumika Bayer Urethane K.K.) and 58.7 parts by weight of SUMIFEN 1600U (linear polyether polyol manufactured by Sumika Bayer Urethane K.K.) were mixed uniformly to afford Polyol premix 2. The viscosity of Polyol premix 2 was 282 m·Pa (B type viscometer, 25° C., 12 rpm, Rotor No. 1).

Reference Example 5 (Preparation of Polyol Premix 3)

31.2 parts by weight of SUMIFEN TM (branched polyether polyol manufactured by Sumika Bayer Urethane K.K.) and 68.8 parts by weight of SUMIFEN 1600U (linear polyether polyol manufactured by Sumika Bayer Urethane K.K.) were mixed uniformly to afford Polyol premix 3. The viscosity of Polyol premix 3 was 277 m·Pa (B type viscometer, 25° C., 12 rpm, Rotor No. 1).

Reference Example 6 (Preparation of Polyol Premix 4)

19.9 parts by weight of ethylene glycol (manufactured by Nippon Shokubai Co., Ltd.) and 80.1 parts by weight of SUMIFEN 1600U (linear polyether polyol manufactured by Sumika Bayer Urethane K.K.) were mixed uniformly to afford Polyol premix 4. The viscosity of Polyol premix 4 was 176 m·Pa (B type viscometer, 25° C., 12 rpm, Rotor No. 1).

Production Example 1

Into the vessel of the above-described HIGH SPEED MIXER apparatus was charged 100 parts by weight of Powdery pesticide 1, and the agitator blade (revolution: 1800 rpm) and the chopper blade (revolution: 2000 rpm) of the apparatus were rotated. In the apparatus, the powdery pesticide was stirred by the agitator all in the condition of rolling, and intense shearing force was applied to the powdery pesticide mainly by the chopper blade. Next, the vessel was heated, and 1.55 parts by weight of Polyol premix 1 was added while maintaining the temperature of the powdery pesticide at 75±5° C. The scene of Polyol premix 1 of infiltration into the powdery pesticide was observed. Three minutes after, 0.95 parts by weight of polyisocyanate {SUMIDUL 44V10 (polymethylene polyphenyl polyisocyanate manufactured by Sumika Bayer Urethane K.K.), viscosity: 130 m·Pa (25° C.)} was added while maintaining the temperature of the powdery pesticide at 75±5° C. From directly after addition, a thickening phenomenon was confirmed, and thereafter, the viscosity lowered, and hardening of the polyurethane resin was observed (corresponding to 2.5 parts by weight of the polyurethane resin relative to 100 parts by weight of the powdery pesticide).

Further, 5 minutes after, operations of 1) addition of 1.55 parts by weight of Polyol premix 1, 2) continuance of stirring and mixing for 3 minutes, 3) addition of 0.95 parts by weight of a polyisocyanate and 4) continuance of stirring and mixing for 5 minutes were repeated 3 times while continuing stirring maintaining the temperature in the HIGH SPEED MIXER apparatus at 75±5° C., and thereafter, the mixture was left to cool, to afford pesticidal granules of the present invention.

Thus, pesticidal granules of the present invention was obtained using polyurethane resin raw materials in a total amount of 10 parts by weight relative to 100 parts by weight of the powdery pesticide (addition frequency of urethane resin raw material: 4 times, addition amount of urethane resin raw material per one addition: 2.5 parts by weight, total addition amount of urethane resin raw materials: 10 parts by weight).

Production Examples 2 to 6

According to the same procedure as in Production Example 1, pesticidal granules of the present invention were obtained by adding urethane resin raw materials in an amount of 2.5 parts by weight per one addition for addition frequencies described in Table 1.

TABLE 1

| | Powdery peststicide 1 (part by weight) | Addition amount of resin raw material (*) per one addition (part by weight) | Addition frequency of resin raw material (*) | Total addition amount of resin raw material (part by weight) |
| --- | --- | --- | --- | --- |
| Production Example 1 | 100 | 2.5 | 4 times | 10 |

TABLE 1-continued

| | Powdery peststicide 1 (part by weight) | Addition amount of resin raw material (*) per one addition (part by weight) | Addition frequency of resin raw material (*) | Total addition amount of resin raw material (part by weight) |
|---|---|---|---|---|
| Production Example 2 | 100 | 2.5 | 8 times | 20 |
| Production Example 3 | 100 | 2.5 | 12 times | 30 |
| Production Example 4 | 100 | 2.5 | 16 times | 40 |
| Production Example 5 | 100 | 2.5 | 20 times | 50 |
| Production Example 6 | 100 | 2.5 | 22 times | 55 |

(*) Resin raw material means urethane resin raw material, and amount thereof is sum of polyol premix and polyisocyanate.

Test Example 1

1) Measurement of Average Particle Size

The volume median diameters of the pesticidal granules of the present invention obtained in Production Examples 1 to 6 were measured by MASTERSIZER 2000 manufactured by MALVERN. The results are shown in Table 2.

2) Elution Test

Powdery pesticide 1 and the pesticidal granules of the present invention obtained in Production Examples 1 to 6 were taken in an amount of 5 mg in terms of 5-chloro-N-(1,3-dihydro-1,1,3-trimethyl-4-isobenzofuranyl)-1,3-dimethylpyrazole-4-carboxamide into a 100 ml screw tube, and 100 g of ion-exchanged water was added to this and the mixture was allowed to stand for 24 hours in a constant temperature chamber of 25° C. Thereafter, solid components were filtrated off through a filter, and the amount of 5-chloro-N-(1,3-dihydro-1,1,3-trimethyl-4-isobenzofuranyl)-1,3-dimethylpyrazole-4-carboxamide eluted into water was measured, and the proportion of elution into water (elution ratio) was calculated. The results are shown in Table 2.

TABLE 2

| | Volume median diameter (μm) | Elution ratio (%) After 1 day | Elution ratio (%) After 3 days |
|---|---|---|---|
| Powdery pesticide 1 | 5.0 | 85 | 100 |
| Production Example 1 | 34.7 | 80 | 90 |
| Production Example 2 | 36.9 | 74 | 88 |
| Production Example 3 | 40.9 | 45 | 80 |
| Production Example 4 | 43.1 | 41 | 73 |
| Production Example 5 | 44.8 | 39 | 69 |
| Production Example 6 | 45.0 | 36 | 56 |

Production Example 7

Into the vessel of the above-described HIGH SPEED MIXER apparatus was charged 100 parts by weight of Powdery pesticide 2, and the agitator blade (revolution: 1800 rpm) and the chopper blade (revolution: 2000 rpm) of the apparatus were rotated. In the apparatus, the powdery pesticide was stirred by the agitator all in the condition of rolling, and intense shearing force was applied to the powdery pesticide mainly by the chopper blade. Next, the vessel was heated, and 1.55 parts by weight of Polyol premix 1 was added while maintaining the temperature of the powdery pesticide at 75±5° C. The scene of Polyol premix 1 of infiltration into the powdery pesticide was observed. Three minutes after, 0.95 parts by weight of polyisocyanate {SUMIDUL 44V10 (polymethylene polyphenyl polyisocyanate manufactured by Sumika Bayer Urethane K.K.)} was added while maintaining the temperature of the powdery pesticide at 75±5° C. From directly after addition, a thickening phenomenon was confirmed, and thereafter, the viscosity lowered, and hardening of the polyurethane resin was observed (corresponding to 2.5 parts by weight of the polyurethane resin relative to 100 parts by weight of the powdery pesticide).

Further, 5 minutes after, operations of 1) addition of 1.55 parts by weight of the polyol premix 1, 2) continuance of stirring and mixing for 3 minutes, 3) addition of 0.95 parts by weight of a polyisocyanate and 4) continuance of stirring and mixing for 5 minutes were repeated 19 times while continuing stirring maintaining the temperature in the HIGH SPEED MIXER apparatus at 75±5° C., and thereafter, the mixture was left to cool, to afford pesticidal granules of the present invention.

Thus, pesticidal granules of the present invention were obtained using polyurethane resin raw materials in a total amount of 50 parts by weight relative to 100 parts by weight of Powdery pesticide 2 (addition frequency of urethane resin raw material: 20 times, addition amount of urethane resin raw material per one addition: 2.5 parts by weight, total addition amount of urethane resin raw materials: 50 parts by weight).

Production Examples 8 to 11

According to the same procedure as in Production Example 7, pesticidal granules of the present invention were obtained by adding urethane resin raw materials in an amount of 2.5 parts by weight per one addition for addition frequencies described in Table 3.

TABLE 3

| | Powdery pesticidal 2 (part by weight) | Addition amount of resin raw material (*) per one addition (part by weight) | Addition frequency of resin raw material (*) | Total addition amount of resin raw material (part by weight) |
|---|---|---|---|---|
| Production Example 7 | 100 | 2.5 | 20 times | 50 |
| Production Example 8 | 100 | 2.5 | 24 times | 60 |
| Production Example 9 | 100 | 2.5 | 28 times | 70 |
| Production Example 10 | 100 | 2.5 | 32 times | 80 |
| Production Example 11 | 100 | 2.5 | 40 times | 100 |

(*) Resin raw material means urethane resin raw material, and amount thereof is sum of polyol premix and polyisocyanate.

Test Example 2

1) Measurement of Average Particle Size

The volume median diameters of the pesticidal granules of the present invention obtained in Production Examples 7 to 11 were measured by MASTERSIZER 2000 manufactured by MALVERN. The results are shown in Table 4.

2) Elution Test

The powdery pesticide and the pesticidal granules of the present invention obtained in Production Examples 7 to 11 were taken in an amount of 5 mg in terms of (E)-N-(6-chloro-3-pyridylmethyl)-N-ethyl-N'-methyl-2-nitrovinylidenediamine into a 100 ml screw tube, and 100 g of ion-exchanged water was added to this and the mixture was allowed to stand for 24 hours in a constant temperature chamber of 25° C. Thereafter, solid components were filtrated off through a filter, and the amount of (E)-N-(6-chloro-3-pyridylmethyl)-N-ethyl-N'-methyl-2-nitrovinylidenediamine eluted into water was measured, and the proportion of elution into water (elution ratio) was calculated. The results are shown in Table 4.

TABLE 4

| | Volume median diameter (μm) | Elution ratio (%) | |
|---|---|---|---|
| | | After 1 day | After 3 days |
| Powdery pesticide 2 | 16.0 | 100 | 100 |
| Production Example 7 | 53.3 | 86 | 90 |
| Production Example 8 | 52.3 | 77 | 84 |
| Production Example 9 | 57.4 | 23 | 51 |
| Production Example 10 | 57.9 | 12 | 23 |
| Production Example 11 | 61.5 | 3 | 5 |

Production Example 12

Into the vessel of the above-described HIGH SPEED MIXER apparatus is charged 100 parts by weight of Powdery pesticide 1, and the agitator blade (revolution: 850 rpm) and the chopper blade (revolution: 2000 rpm) of the apparatus are rotated. Next, the mixing vessel is heated, and 1.55 parts by weight of Polyol premix 1 is added while maintaining the temperature of the powdery pesticide at 75±5° C. Three minutes after, 0.95 parts by weight of polyisocyanate {SUMIDUL 44V10 (polymethylene polyphenyl polyisocyanate manufactured by Sumika Bayer Urethane K.K.)} is added while maintaining the temperature of the powdery pesticide at 75±5° C. (corresponding to 2.5 parts by weight of the polyurethane resin relative to 100 parts by weight of the powdery pesticide).

Further, 5 minutes after, operations of 1) addition of 1.55 parts by weight of Polyol premix 1, 2) continuance of stirring and mixing for 3 minutes, 3) addition of 0.95 parts by weight of a polyisocyanate and 4) continuance of stirring and mixing for 5 minutes are repeated 19 times while continuing stirring maintaining the temperature in the HIGH SPEED MIXER apparatus at 75±5° C., and thereafter, the mixture is left to cool, to afford pesticidal granules of the present invention.

Thus, pesticidal granules of the present invention are obtained using polyurethane resin raw materials in a total amount of 50 parts by weight relative to 100 parts by weight of the powdery pesticide (addition frequency of urethane resin raw material: 20 times, addition amount of urethane resin raw material per one addition: 2.5 parts by weight, total addition amount of urethane resin raw materials: 50 parts by weight).

The resultant pesticidal granules have a larger average particle size as compared with the pesticidal granules of the present invention obtained in Production Example 5.

Production Example 13

Into the vessel of the above-described HIGH SPEED MIXER apparatus is charged 100 parts by weight of Powdery pesticide 1, and the agitator blade (revolution: 1800 rpm) and the chopper blade (revolution: 2000 rpm) of the apparatus are rotated. Next, the mixing vessel is heated, and 1.65 parts by weight of Polyol premix 2 is added while maintaining the temperature of the powdery pesticide at 75±5° C. Three minutes after, 0.85 parts by weight of polyisocyanate {SUMIDUL 44V10 (polymethylene polyphenyl polyisocyanate manufactured by Sumika Bayer Urethane K.K.)} is added while maintaining the temperature of the powdery pesticide at 75±5° C. (corresponding to 2.5 parts by weight of the polyurethane resin relative to 100 parts by weight of the powdery pesticide).

Further, 5 minutes after, operations of 1) addition of 1.65 parts by weight of Polyol premix 2, 2) continuance of stirring and mixing for 3 minutes, 3) addition of 0.85 parts by weight of a polyisocyanate and 4) continuance of stirring and mixing for 5 minutes are repeated 19 times while continuing stirring maintaining the temperature in the HIGH SPEED MIXER apparatus at 75±5° C., and thereafter, the mixture is left to cool, to afford pesticidal granules of the present invention.

Thus, pesticidal granules of the present invention are obtained using polyurethane resin raw materials in a total amount of 50 parts by weight relative to 100 parts by weight of the powdery pesticide (addition frequency of urethane resin raw material: 20 times, addition amount of urethane resin raw material per one addition: 2.5 parts by weight, total addition amount of urethane resin raw materials: 50 parts by weight).

The resultant pesticidal granules give faster elution of 5-chloro-N-(1,3-dihydro-1,1,3-trimethyl-4-isobenzofuranyl)-1,3-dimethylpyrazole-4-carboxamide as compared with the pesticidal granules of the present invention obtained in Production Example 5.

Production Example 14

Into the vessel of the above-described HIGH SPEED MIXER apparatus is charged 100 parts by weight of Powdery pesticide 1, and the agitator blade (revolution: 1800 rpm) and the chopper blade (revolution: 2000 rpm) of the apparatus are rotated. Next, the mixing vessel is heated, and 1.71 parts by weight of Polyol premix 3 is added while maintaining the temperature of the powdery pesticide at 75±5° C. Three minutes after, 0.79 parts by weight of polyisocyanate {SUMIDUL 44V10 (polymethylene polyphenyl polyisocyanate manufactured by Sumika Bayer Urethane K.K.)} is added while maintaining the temperature of the powdery pesticide at 75±5° C. (corresponding to 2.5 parts by weight of the polyurethane resin relative to 100 parts by weight of the powdery pesticide).

Further, 5 minutes after, operations of 1) addition of 1.71 parts by weight of Polyol premix 3, 2) continuance of stirring and mixing for 3 minutes, 3) addition of 0.79 parts by weight of a polyisocyanate and 4) continuance of stirring and mixing for 5 minutes are repeated 19 times while continuing stirring maintaining the temperature in the HIGH SPEED MIXER apparatus at 75±5° C., and thereafter, the mixture was left to cool, to afford pesticidal granules of the present invention.

Thus, pesticidal granules of the present invention are obtained using polyurethane resin raw materials in a total amount of 50 parts by weight relative to 100 parts by weight of the powdery pesticide (addition frequency of urethane resin raw material: 20 times, addition amount of urethane resin raw material per one addition: 2.5 parts by weight, total addition amount of urethane resin raw materials: 50 parts by weight).

The resultant pesticidal granules give faster elution of 5-chloro-N-(1,3-dihydro-1,1,3-trimethyl-4-isobenzofuranyl)-1,3-dimethylpyrazole-4-carboxamide as compared with the pesticidal granules of the present invention obtained in Production Example 5.

Production Example 15

Into the vessel of the above-described HIGH SPEED MIXER apparatus is charged 100 parts by weight of Powdery pesticide 1, and the agitator blade (revolution: 1800 rpm) and the chopper blade (revolution: 2000 rpm) of the apparatus are rotated. Next, the mixing vessel is heated, and 3.10 parts by weight of Polyol premix 1 is added while maintaining the temperature of the powdery pesticide at 75±5° C. Three minutes after, 1.90 parts by weight of polyisocyanate {SUMIDUL 44V10 (polymethylene polyphenyl polyisocyanate manufactured by Sumika Bayer Urethane K.K.)} is added while maintaining the temperature of the powdery pesticide at 75±5° C. (corresponding to 5.0 parts by weight of the polyurethane resin relative to 100 parts by weight of the powdery pesticide).

Further, 5 minutes after, operations of 1) addition of 3.10 parts by weight of Polyol premix 1, 2) continuance of stirring and mixing for 3 minutes, 3) addition of 1.90 parts by weight of a polyisocyanate and 4) continuance of stirring and mixing for 5 minutes are repeated 19 times while continuing stirring maintaining the temperature in the HIGH SPEED MIXER apparatus at 75±5° C., and thereafter, the mixture is left to cool, to afford pesticidal granules of the present invention.

Thus, pesticidal granules of the present invention are obtained using polyurethane resin raw materials in a total amount of 50 parts by weight relative to 100 parts by weight of the powdery pesticide (addition frequency of urethane resin raw material: 10 times, addition amount of urethane resin raw material per one addition: 5.0 parts by weight, total addition amount of urethane resin raw materials: 50 parts by weight).

The resultant pesticidal granules give slower elution of 5-chloro-N-(1,3-dihydro-1,1,3-trimethyl-4-isobenzofuranyl)-1,3-dimethylpyrazole-4-carboxamide as compared with the pesticidal granules of the present invention obtained in Production Example 5.

Production Example 16

Into the vessel of the above-described HIGH SPEED MIXER apparatus is charged 100 parts by weight of Powdery pesticide 1, and the agitator blade (revolution: 1800 rpm) and the chopper blade (revolution: 2000 rpm) of the apparatus are rotated. Next, the mixing vessel is heated, and 1.20 parts by weight of Polyol premix 4 is added while maintaining the temperature of the powdery pesticide at 75±5° C. Three minutes after, 1.30 parts by weight of polyisocyanate {SUMIDUL 44V10 (polymethylene polyphenyl polyisocyanate manufactured by Sumika Bayer Urethane K.K.)} is added while maintaining the temperature of the powdery pesticide at 75±5° C. (corresponding to 2.5 parts by weight of the polyurethane resin relative to 100 parts by weight of the powdery pesticide).

Further, 5 minutes after, operations of 1) addition of 1.20 parts by weight of Polyol premix 4, 2) continuance of stirring and mixing for 3 minutes, 3) addition of 1.30 parts by weight of a polyisocyanate and 4) continuance of stirring and mixing for 5 minutes are repeated 19 times while continuing stirring maintaining the temperature in the HIGH SPEED MIXER apparatus at 75±5° C., and thereafter, the mixture is left to cool, to afford pesticidal granules of the present invention.

Thus, pesticidal granules of the present invention are obtained using polyurethane resin raw materials in a total amount of 50 parts by weight relative to 100 parts by weight of the powdery pesticide (addition frequency of urethane resin raw material: 20 times, addition amount of urethane resin raw material per one addition: 2.5 parts by weight, total addition amount of urethane resin raw materials: 50 parts by weight).

Production Example 17

Into the vessel of the above-described HIGH SPEED MIXER apparatus is charged 100 parts by weight of Powdery pesticide 1, and the agitator blade (revolution: 1800 rpm) and the chopper blade (revolution: 2000 rpm) of the apparatus were rotated. Next, the mixing vessel is heated, and 0.83 parts by weight of a polyamine mixture (E206W hardening agent, manufactured by Konishi K.K., viscosity: 400 m·Pa (25° C.)) is added while maintaining the temperature of the powdery pesticide at 75±5° C. Three minutes after, 1.67 parts by weight of polyglycidyl ether (E206W main agent, manufactured by Konishi K.K., bisphenol F type epoxy main agent, viscosity: 500 m·Pa (25° C.)) is added while maintaining the temperature of the powdery pesticide at 75±5° C. (corresponding to 2.5 parts by weight of the epoxy resin relative to 100 parts by weight of the powdery pesticide).

Further, 5 minutes after, operations of 1) addition of 0.83 parts by weight of E206W hardening agent, 2) continuance of stirring and mixing for 3 minutes, 3) addition of 1.67 parts by weight of E206W main agent and 4) continuance of stirring and mixing for 5 minutes are repeated 19 times while continuing stirring maintaining the temperature in the HIGH SPEED MIXER apparatus at 75±5° C., and thereafter, the mixture is left to cool, to afford pesticidal granules of the present invention.

Thus, pesticidal granules of the present invention are obtained using epoxy resin raw materials in a total amount of 50 parts by weight relative to 100 parts by weight of the powdery pesticide (addition frequency of epoxy resin raw material: 20 times, addition amount of epoxy resin raw material per one addition: 2.5 parts by weight, total addition amount of epoxy resin raw materials: 50 parts by weight).

INDUSTRIAL APPLICABILITY

The pesticidal granule of the present invention is capable of enabling a pesticidal active ingredient to be controlled-released. The production method of the present invention is capable of easily providing a pesticidal composition containing an pesticidal active ingredient in a controlled-release form.

The invention claimed is:

1. A method for producing a pesticidal composition comprising
a process of mixing a powdery pesticide with a first liquid component serving as a raw material for a thermosetting resin,
a process of adding a second liquid component serving as a raw material for a thermosetting resin, and then
making the first liquid component react with the second liquid component to produce a thermosetting resin.

2. The method for producing a pesticidal composition according to claim 1, which comprises a process of mixing a powdery pesticide with a first liquid component serving as a raw material for a thermosetting resin, a process of adding a second liquid component serving as a raw material for a thermosetting resin, obtaining a pesticidal granule by making the first liquid component react with the second liquid component to produce a thermosetting resin, a process of adding to the resultant pesticidal granule the first liquid component and the second liquid component simultaneously or sequentially, and then making them react for coating of the pesticidal granule with the thermosetting resin.

3. The method for producing a pesticidal composition according to claim 1, wherein the powdery pesticide is a powdery pesticide comprising 5-chloro-N-(1,3-dihydro-1,1,3-trimethyl-4-isobenzofuranyl)-1,3-dimethylpyrazole-4-carboxamide as a pesticidal active ingredient.

4. The method for producing a pesticidal composition according to claim 1, wherein the powdery pesticide is a powdery pesticide comprising (E)-N-(6-chloro-3-pyridylmethyl)-N-ethyl-N'-methyl-2-nitrovinylidenediamine as a pesticidal active ingredient.

5. The method for producing a pesticidal composition according to claim 1, wherein the thermosetting resin is a urethane resin, urea resin or epoxy resin.

6. The method for producing a pesticidal composition according to claim 1, wherein the thermosetting resin is a urethane resin.

7. The method for producing a pesticidal composition according to claim 6, wherein the first liquid component is a polyol and the second liquid component is a polyisocyanate.

8. The method for producing a pesticidal composition according to claim 1, wherein the thermosetting resin is an epoxy resin.

9. The method for producing a pesticidal composition according to claim 8, wherein the first liquid component is a polyamine and the second liquid component is a polyglycidyl ether or polyglycidylamine.

10. The method according to claim 1, wherein the powdery pesticide has an average particle size of 1 to 100 μm.

11. The method according to claim 1, wherein the powdery pesticide has an average particle size of 1 to 30 μm.

12. The method according to claim 1, wherein the method is carried out in the absence of a solvent.

* * * * *